United States Patent [19]

Henson

[11] Patent Number: 5,728,924

[45] Date of Patent: Mar. 17, 1998

[54] INBRED CORN LINE NP 934

[76] Inventor: Allen R. Henson, 3393 County Rd. 800 E., Dewey, Ill. 61840

[21] Appl. No.: 690,252

[22] Filed: Jul. 24, 1996

Related U.S. Application Data

[63] Continuation of Ser. No. 375,033, Jan. 19, 1995.

[51] Int. Cl.$^6$ .............................. A01H 5/00; A01H 4/00; C12N 5/04
[52] U.S. Cl. ................. 800/200; 800/250; 800/DIG. 56; 47/58; 47/DIG. 1; 435/424; 435/430; 435/430.1; 435/412
[58] Field of Search ..................... 800/200, 205, 800/235, 250, DIG. 56; 435/240.1, 240.4, 240.47, 240.49, 240.5; 47/58.01, 58.03

[56] References Cited

U.S. PATENT DOCUMENTS 5,276,260  1/1994  Foley ........................ 800/200

OTHER PUBLICATIONS

Phillips et al. In Corn and Corn Improvement. Third Edition. Sprague et al. eds. Chapter 5: 345–387, 1988.

*Primary Examiner*—Gary Benzion
*Assistant Examiner*—Melissa L. Kimball
*Attorney, Agent, or Firm*—Thomas Hoxie

[57] ABSTRACT

An inbred corn line, designated NP 934, is disclosed. The invention relates to the seeds of inbred corn line NP 934, to the plants of inbred corn line NP 934 and to methods for producing a corn plant produced by crossing inbred line NP 934 with itself or with another corn plant. The invention further relates to hybrid corn seeds and plants produced by crossing inbred line NP 934 with another corn line. Particularly the invention provides a novel hybrid corn plant, designated N7992 produced by crossing inbred NP 934 with another Northrup King proprietary inbred corn line.

16 Claims, No Drawings

INBRED CORN LINE NP 934

This is a continuation of application Ser. No. 08/375,033, filed on Jan. 19, 1995.

BACKGROUND OF THE INVENTION

This invention relates to the field of corn breeding. More specifically the invention is related to a new and distinctive corn inbred line designated NP 934 and to hybrids made by using NP 934 as a parent.

Corn is a valuable and important field crop. Thus, plant breeders are continually developing new and superior corn inbred lines for production of high yielding, agronomicly sound hybrids. The goal of the plant breeder is to maximize the amount of corn grain produced and to minimize the plant's susceptibility to environmental and pest stresses.

Corn hybrid development requires the development of homozygous inbred lines, the crossing of these lines, and the subsequent evaluation of those crosses. Pedigree, backcross, and recurrent selection breeding methods are used to develop inbred lines from breeding populations. Breeding programs combine the genetic backgrounds from two or more inbred lines or various other genetic sources into breeding pools from which new inbred lines are developed by self pollination and selection of desired phenotypes. The new inbred lines are crossed with other inbred lines, and hybrids from these crosses are evaluated to determine which have commercial potential.

Once the inbred parents that give a superior hybrid are identified, the hybrid seed can be reproduced indefinitely as long as inbred parent homogeneity is maintained. Corn hybrids may be either single cross hybrids, produced when two inbred lines are crossed to produce the $F_1$ progeny; or double cross hybrids, produced from four inbred lines crossed in pairs (A×B and C×D) and then the two $F_1$ hybrids are crossed again (A×B)×(C×D); or three way cross hybrids produced by crossing a single cross (A×B) to a third inbred (C). Numerous references are available on the topic of corn breeding and hybrid seed corn production.

Those skilled in the art of corn breeding and production are well aware of techniques and methods for the development of inbred corn lines and corn hybrids. Reference is made particularly to Corn and Corn Improvement, Third Edition, eds. G. F. Sprague and J. W. Dudley, American Society of Agronomy Monograph No. 18, particularly chapters 8 and 9.

SUMMARY OF THE INVENTION

The invention provides a novel inbred corn line 934, designated NP 934. This invention thus relates to the seeds of inbred corn line NP 934, to the plants of inbred corn line NP 934 and to methods of producing a corn plant produced by the crossing of inbred line NP 934 with itself or another corn line. This invention further relates to hybrid corn seeds and plants produced by crossing the inbred line NP 934 with another corn inbred line.

DEFINITIONS

In the description and examples that follow a number of terms are used; therefore, to provide a clear and consistent understanding of the specification and claims the following definitions are provided.

RK=Round Kernels: the percentage of kernels that do not pass through a 13/64 slotted screen.

HE=Husk Extension: the length (cm) of the husk past the ear tip at maturity.

LL=Leaf Length: the length of the ear leaf measured in cm.

NN=Node Number: the number of nodes of the entire plant.

PRM=Predicted Relative Maturity. This trait is based on the harvest moisture of the grain. The relative maturity rating is based on a known set of checks.

MST=Harvest Moisture. The moisture is the actual percentage moisture of the grain at harvest.

STK (BR)=The percentage of plants broken below the ear at harvest.

YLD=Yield; bushels per acre. The actual yield of the grain at harvest (bu/a) adjusted to 15.5% moisture.

RT=Number of plants lodged (leaning from vertical but not broken).

DETAILED DESCRIPTION OF THE INVENTION

Inbred corn line NP 934 is a yellow dent inbred line with superior characteristics and is best suited as a male in crosses for production of first generation $F_1$ corn hybrids. NP 934 is best adapted to the Southern Cornbelt Area of the United States, and can be used to produce hybrids from approximately 112 to 125 days relative maturity based on the Minnesota Relative Maturity Rating System for harvest of grain.

Inbred corn line NP 934 was developed from the $F_1$ population (LH123×J8503) by self-pollination and simple pedigreed ear-to-row breeding. Parent LH123 is a well known Holden's Foundation Seed Co. inbred line, and parent J8503 is a Northrup King Co. line derived by selfing within the $F_1$ of Pioneer P3382. Self-pollination and selection were practiced within the above $F_1$ cross for seven generations in the development of NP 934. During the development of the line, crosses of segregating families were made to inbred testers to evaluate combining ability. Inbred line NP 934 can be reproduced by planting seeds of the line, growing the resulting corn plants under self-pollination or sib-pollination conditions with adequate isolation and then harvesting the resulting seed. No variant traits have been observed or are expected in NP 934.

Inbred line NP 934 has been evaluated at numerous research stations across the United States Corn Belt. The line is uniform and stable for all discernible characteristics as described in the following Variety Description, Table 1. The description is based on data collected primarily at Phillips, Nebr. and St. Joseph, Ill. on a maximum of 4 replications and or 10 subsamples. In interpreting the color designation herein, reference is made to the Munsell Glossy Book of Color, a standard color reference.

TABLE 1

VARIETY DESCRIPTION INFORMATION FOR INBRED LINE NP 934

Type: Dent   Region Best Adapted: Southern Corn Belt (US)
A. Maturity:

Heat Units Silk (HUS): 1489.

$$\text{Heat Units} = \frac{\text{Max Temp} (\leq 86° \text{F.}) + \text{Min Temp} (\geq 50° \text{F.})}{2} - 50$$

TABLE 1-continued

VARIETY DESCRIPTION INFORMATION FOR INBRED LINE NP 934

Type: Dent    Region Best Adapted: Southern Corn Belt (US)
B. Plant Characteristics:

Plant height (to tassel tip): 268 cm
Length to top ear internode: 14 cm
Ear height (to base of top ear internode): 99 cm
Number of tillers: none
Number of ears per stalk: 2.7
Cytoplasm type: normal C. Leaf:

Color: medium green
Angle from stalk (upper half): 30 degrees
Number of leaves (mature plants): above top of the ear (7)
Marginal waves: few
Width (widest point of ear node leaf): 8.3 cm
Sheath Pubescence: few
Longitudinal creases: few
Length (ear node leaf, "LL"): 89 cm D. Tassel:

Number of lateral branches: 5
Branch angle from central spike: 30 degrees
Pollen shed: light
Peduncle length (top leaf to basal branch): 6 cm
Anther color: green-yellow
Glume color: green-yellow E. Ear (Husked ear data except where stated otherwise):

Length: 13 cm
Weight: 95 gm
Midpoint diameter: 37 mm
Kernel rows: 14
Silk color: green-yellow
Husk extension: long
Taper of ear: average
Husk color (fresh): medium green
Husk color (dry): tan
Shank length: 10.4 cm
Shank (no. of internodes): 9

F. Kernel (Dried):

Size (from ear mid-point):
Length: 10 mm
Width: 7 mm
Thickness: 4.1 mm
Shape grade (% rounds): 30%
Pericarp color: colorless
Aleurone color: colorless
Endosperm color: yellow-orange
Endosperm type: normal starch
Gm weight/100 seeds (unsized): 27

G. Cob:

Diameter at mid-point: 23 mm
Strength: strong
Color: light red

H. Disease Resistance and Insect Resistance:

Preliminary data suggest
Northern leaf blight: resistant
Southern corn leaf blight: susceptible
European corn borer: susceptible J. Variety Most Closely Resembling:

| Character | Inbred |
|---|---|
| Maturity | Mo17 |
| Usage | Mo17 |

Inbred Mo17 is a well known and available corn line. Inbred corn line NP 934 may be distinguished from Mo17 and other inbred lines by characteristics described in Table 2.

TABLE 2

1994 Variety Comparison Data of Inbred Line NP 934

| Variety/Line | Silk HU | Pollen HU | Plant Ht.(cm) | Ear Ht.(cm) |
|---|---|---|---|---|
| NP 934 | 1569 | 1576 | 266 | 92 |
| Mo17 | 1582 | 1476 | 220 | 83 |
| NP 5304 | 1572 | 1546 | 228 | 86 |
| B73 | 1513 | 1502 | 235 | 97 |
| B68 | 1628 | 1567 | 227 | 89 |
| # Reps | 10 | 10 | 8 | 8 |
| LSD(0.5) | 43 | 41 | 18 | 12 |
| cv % | 3 | 3 | 7 | 12 |

This invention is also directed to methods for producing a corn plant by crossing a first parent corn plant with a second parent corn plant, wherein the first or second corn plant is a corn plant of the inbred line NP 934. However, both first and second parent corn plant can come from the inbred corn line NP 934. Therefore any methods using NP 934 are part of this invention including self-pollination, backcross-pollination, hybrid breeding and crosses to populations. Any plants produced using inbred corn line NP 934 as a parent are within the scope of this invention including any plant produced by the use of cells, protoplasts or tissue from NP 934.

An example of a hybrid produced by crossing inbred line NP 934 is N7992. This hybrid has NP 934 as a male parent and Northrup King inbred line NP 8304 as a female parent. Inbred NP 8304 (also known as W8304) has PVP Certificate No. 8800032 which is hereby incorporated by reference. The techniques used to obtain the corn hybrid seeds and plants are conventional in the seed industry and are well known to those skilled in the art. The two parent lines are planted in pollinating proximity to each other in alternating sets of rows; however, any convenient planting pattern that allows for the free transfer of pollen is acceptable. The plants of both inbred lines are allowed to grow until the time of flowering. At flowering, the tassels are removed from all plants of the female parent. Natural cross-pollination is allowed to occur. Only the ears from the female plants, NP 8304, are harvested to obtain novel $F_1$ hybrid corn seeds N7992 of the present invention. The $F_1$ hybrid corn plants of the invention are obtained by planting the seeds of N7992 at the next proper growing season. The techniques used to obtain the corn hybrid seeds and plants are conventional in the seed industry and are well known to those skilled in the art.

N7992 is a 120 relative maturity (RM) single cross hybrid. N7992 most closely resembles Northrup King Co. hybrid N7989. N7989 is a Northrup King Co. hybrid sold in the Southern Corn Belt and Southeast U.S. N7992 is substantially higher yielding than N7989. N7992 silks about 50 HU sooner than N7989, with comparable plant and ear height. N7992 has been compared with various hybrids. In Table 3 some of these results are indicated for N7992 compared to N7989.

TABLE 3

Combined Location and Year Performance Data
(1993–1994: Corn Belt Locations Nebraska to Ohio)

| Hybrid | YLD (bu/a) | MST | STK (BR) % | RT | HU | Plant Ht. (cm) | DE # |
|---|---|---|---|---|---|---|---|
| N7992 | 163 | 22.6 | 3 | 2 | 1485 | 281 | 25 |
| N7989 | 146 | 23.1 | 5 | 2 | 1536 | 269 | 33 |
| P3394 | 159 | 18.9 | 4 | 2 | 1425 | 260 | 21 |
| N7707 | 162 | 22.0 | 3 | 1 | 1436 | 268 | 25 |
| P3245 | 156 | 20.4 | 5 | 1 | 1470 | 269 | 15 |
| LSD | 5 | 0.4 | 1 | 3 | 17 | 5 | 0 |

N7992 may be further described by characteristics listed in Table 4.

TABLE 4

VARIETY DESCRIPTION INFORMATION FOR HYBRID N7992

Type: Dent    Region Best Adapted: Southern Corn Belt
             (Northrup King Maturity Zone 7)

A. Maturity:

Relative Maturity (RM): 116–120 days
  U.S. Heat Units = 2720–2800
  FAO = 600–700
  Cytoplasm Type: normal B. Preflowering:

Length of first leaf blade: long
  Anthocyanic pigment of seedling: medium
  Juvenile plant:

color: medium green
    form: planofil
    size: medium

C. Flowering

Number of leaves: 16 below ear: 9
  above ear: 7
  Leaf angle from stalk: 30–60 degrees
  Leaf:

marginal waves: few
    longitudinal creases: few
    color: dark
    Number of tillers: None
    Plant height to tassel tip: 310 cm
    Length of top ear internode: 20 cm
    Second internode:

width: 24 mm
      length: 8 cm
      Anthocyanic pigment of brace roots: medium
      Shape of tassel: loose
      Number of lateral tassel branches: 7
      Tassel branch angle: 30–45 degrees from vertical
      Length of largest tassel branch: medium
      Anther color: yellow
      Heat units to:

50% pollen shed: 1472
        50% silk: 1448
        Silk:

color: green
          length outside of husk: 4 cm
          Fresh husk color: light green
          Ear leaf:

anthocyanic pigment: weak or none
            pubescence: medium
            sheath pubescence: light or none

TABLE 4-continued

VARIETY DESCRIPTION INFORMATION FOR HYBRID N7992

Type: Dent    Region Best Adapted: Southern Corn Belt
             (Northrup King Maturity Zone 7)

length: 95 cm
  width: 11 cm
  Ear height: 125 cm
  Number of:

nodes: 14
    anthocyanic nodes: 10
    anthocyanic internodes: 3
    nodes with adventitious roots: 2
    Peduncle length: 11 cm
    Central spike length: long
    Glume:

color: green
      band color: green
      Pollen shed: medium
      % of plants with ear wings: 60
      Ear wing length: 2 cm
      Number of ears per stalk: single D. Maturity Husk:

extension: 2 cm
    at maturity (HE): loose
    Shank:

length: 11 cm
      internode number: 8
      Kernel:

rows: distinct
        alignment: straight
        row number: 18
        Ear weight: 231 gm
        Kernel:

100 weight: 31 gm
          length: 12 mm
          width: 8 mm
          thickness: 4 mm
          % round kernels (RK): 14
          Ear:

position at maturity: upright
            length: 19 cm
            diameter: 45 mm
            taper: average
            Cob:

color: red
              diameter: 28 mm
              strength: strong
              Kernel color:

pericarp: colorless
                aleurone segregation: homozygous
                aleurone: tan
                endosperm: yellow
                kernel crown: light yellow
                kernel body (sides): yellow
                Endosperm type: normal
                % of kernels showing purple plumule tip: none As used herein the term plant includes plant cells, plant protoplasts, plant cell tissue cultures including that from which corn plants fertile or otherwise can be regenerated, plant calli and plant cell clumps, and differentiated forms of plants such as, but not limited to embryos, pollen, stamen, anthers, flowers, kernels, ears, cobs, leaves, stalks, roots, shoots, plantlets, silks and kernels.

Methods of cell and tissue culture and regeneration are well known in the art and described for example in "Plant Tissue Culture Manual: Fundamentals and Application", Ed. K. Lindsey, Kluwer (1991) and in Green and Rhodes, "Plant Regeneration in Tissue Culture of Maize", Maize for Biological Research (Plant Molecular Biology Association, Charlottesville, Va., 1982, pp. 367–372), which are hereby incorporated by reference.

As is well known, corn can be put to a wide variety of uses not only as livestock feed but also for human consumption of corn kernels and as a raw material in industry. Both grain and non-grain portions of the plant are used as a livestock feed for swine, cattle and poultry. In the food industry corn is used in wet and dry milling. In wet milling there is the separation of the germ, hull gluten and starch. Germ is used to produce corn oil and germ cake for feed. Corn starch may be packaged for human consumption or used in food products such as sauces, gravies, puddings, sweeteners, syrups, and baking powder. Other nonedible uses include textiles, paper, adhesives, cosmetics, explosives, corn binders, laundry purposes and agricultural formulations. Dry milling is used to produce breakfast foods, grits, cornmeal and corn flour. Other uses of corn include fuel, in the form of fuel alcohol or ethanol; seed; alcoholic beverages and construction.

DEPOSIT INFORMATION

Deposits of at least 2500 seeds each of inbred NP 934 and hybrid N7992 have been made unrestrictedly available to the public via the American Type Culture Collection (ATCC), Rockville, Md. 20852 USA. The deposit corresponds to ATCC Deposit. The deposit of 2500 seeds of the NP 934 was made on Nov. 12, 1997 pursuant to the Budapest Treaty and accorded the deposit number ATCC 209452. The deposit of 2500 seeds of the hybrid N7992 pursuant to the Budapest Treaty was made on Nov. 25, 1997. The seeds are from stock maintained by Northrup King since prior to filing this application. This deposit of Inbred Corn Line NP 934 and Hybrid N7992 will be maintained without restriction in the ATCC depository which is a public depository for a period of 30 years, or 5 years from the most recent request, or for the effective life of the patent, whichever is longer and will be replaced if it becomes nonviable during the period. Additionally, with respect to Plant Variety Protection Certificates received and applied for, Applicant does not waive any infringement of its rights granted under this patent or under the Plant Variety Protection Act (7 U.S.C. 2312 et seq.).

It is claimed:

1. Inbred corn seed designated NP 934 having ATCC Accession No. 209452.

2. A corn plant produced by growing the seed of claim 1.

3. A corn plant having all physiological and morphological characteristics of the plant of claim 2.

4. Pollen of the plant of claim 2.

5. A tissue culture comprising regenerable cells of the plant according to claim 2.

6. A corn plant regenerated from the tissue culture of claim 5, said plant having the capability of expressing all physiological and morphological characteristics of inbred corn plant NP 934, the seed of which has been deposited under ATCC Accession No. 209452.

7. Hybrid seed produced by crossing plants of inbred corn line NP 934, the seed having ATCC accession No. 209452, with plants of another inbred corn line having a genotype different from corn line NP 934.

8. Hybrid plants grown from seed of claim 7.

9. Hybrid seed of claim 7 wherein the inbred corn plant designated NP 934, the seed of which have been deposited and have ATCC Accession No. 209452 is the male parent.

10. A first generation (F1) hybrid corn plant produced by the process of:

a. planting in pollinating proximity seeds of inbred corn line NP 934 having ATCC Accession No: 209452 and a second inbred line;

b. cultivating corn plants resulting from said planting until time of flowering;

c. emasculating the flowers from the second inbred line;

d. allowing cross pollination to occur between said inbreds;

e. harvesting the seeds produced on said plants of the second inbred line; and f. growing the harvested seeds produced in step e.

11. A first generation hybrid corn plant according to claim 10 wherein the hybrid corn plant is the hybrid designated N7992 deposited with ATCC on Nov. 25, 1997.

12. Seeds produced by the cultivation of the hybrid corn plants of claim 10.

13. A tissue culture comprising regenerable cells of the hybrid corn plants of claim 10.

14. $F_1$ generation hybrid corn seed designated N7992 deposited with ATCC on Nov. 25, 1997.

15. $F_1$ generation hybrid corn plants produced by growing the seed of claim 14, said seed deposited with ATCC on Nov. 25, 1997.

16. Seeds produced by the cultivation of the hybrid corn plant of claim 15.

* * * * *